(12) United States Patent
Weed

(10) Patent No.: US 12,268,373 B2
(45) Date of Patent: Apr. 8, 2025

(54) FEMALE URINE COLLECTION AND DRAINAGE DEVICE AND METHODS OF USE THEREOF

(71) Applicant: LampLight Innovations, Inc., Seattle, WA (US)

(72) Inventor: Naomi Ruth Weed, Seattle, WA (US)

(73) Assignee: LampLight Innovations, Inc., Seattle, WA (US)

( * ) Notice: Subject to any disclaimer, the term of this patent is extended or adjusted under 35 U.S.C. 154(b) by 767 days.

(21) Appl. No.: 17/443,405

(22) Filed: Jul. 26, 2021

(65) Prior Publication Data

US 2022/0031290 A1    Feb. 3, 2022

Related U.S. Application Data

(60) Provisional application No. 63/059,380, filed on Jul. 31, 2020.

(51) Int. Cl.
*A61B 10/00* (2006.01)
*A61F 5/455* (2006.01)

(52) U.S. Cl.
CPC .......... *A61B 10/007* (2013.01); *A61F 5/4556* (2013.01)

(58) Field of Classification Search
CPC ....... A61B 10/007; A61F 5/4556; A61F 5/455
See application file for complete search history.

(56) References Cited

U.S. PATENT DOCUMENTS

| | | | | |
|---|---|---|---|---|
| 3,900,019 A * | 8/1975 | Logiadis | ............... | A61B 10/007 4/144.3 |
| 4,194,508 A * | 3/1980 | Anderson | ............... | A61F 5/455 4/144.3 |
| 4,911,698 A * | 3/1990 | Wapner | ............... | A61B 10/007 4/144.3 |
| 4,936,838 A * | 6/1990 | Cross | ............... | A61F 5/455 600/574 |
| 5,687,429 A * | 11/1997 | Rahlff | ............... | A61F 5/455 4/144.4 |
| 7,181,781 B1 * | 2/2007 | Trabold | ............... | A61F 5/455 4/144.1 |
| 2009/0048568 A1 * | 2/2009 | Levinson | ............... | A61F 5/4556 604/329 |

(Continued)

Primary Examiner — Jay B Shah
Assistant Examiner — Andrew E Hoffpauir
(74) Attorney, Agent, or Firm — Levine Bagade Han LLP

(57) ABSTRACT

Disclosed is an improved urine collection and drainage device comprising a device body comprising a vulva-facing portion and a handle portion. The vulva-facing portion can comprise a bulbous protuberance atop a posterior ridge at a posterior end and a partial dome portion in proximity to an anterior end. The urine collection and drainage device can further comprise a urine collection slot defined along a urethra-facing side of the vulva-facing portion in between the bulbous protuberance and the partial dome portion. The bulbous protuberance can be configured to rest against at least part of a vaginal opening, the posterior ridge can be configured to rest against the fourchette of the subject when the urine collection slot surrounds the urethral-opening. The vulva-facing portion can fit snugly against the vulva vestibule such that the labia minora surround the device body to create a watertight seal when pressed against the subject.

23 Claims, 11 Drawing Sheets

(56) References Cited

U.S. PATENT DOCUMENTS

| | | | |
|---|---|---|---|
| 2010/0185168 A1* | 7/2010 | Graauw | A61F 5/4556 604/347 |
| 2011/0028922 A1* | 2/2011 | Kay | A61F 5/455 604/329 |
| 2016/0270767 A1* | 9/2016 | Travers | A61B 10/007 |
| 2019/0247223 A1* | 8/2019 | Brun | A61F 5/453 |

* cited by examiner

FEMALE URINE COLLECTION AND DRAINAGE DEVICE AND METHODS OF USE THEREOF

CROSS-REFERENCE TO RELATED APPLICATION

This application claims the benefit of U.S. Provisional Application No. 63/059,380 filed on Jul. 31, 2020, the content of which is incorporated herein by reference in its entirety.

TECHNICAL FIELD

The present disclosure relates generally to the field of biological sample collection, and, more specifically, to an improved urine collection and drainage device for female patients, primarily used in a healthcare setting. It may also be used outside traditional healthcare settings where females experience barriers to access of toileting facilities.

BACKGROUND

The urinalysis is one of the most commonly-ordered laboratory test in healthcare settings. It is a useful aid not only in diagnosing infections and diseases of urinary system, but other body systems as well. Physicians and healthcare providers order this test when investigating a wide and varied range of physical complaints, such as abdominal pain, back pain, excessive thirst, fevers, and delirium, for example.

For such a routine test, there is currently no simple and efficient process for collecting a urine sample from female patients, especially those with physical and/or cognitive limitations. Furthermore, it is reasonable to assume that most people seeking healthcare fall into the above category for any number of reasons, including illness, injury, physiological processes, pharmacological effects, and exposure to toxic substances.

Most healthcare facilities offer only two options for collecting a urine specimen for urinalysis. One is the "clean catch" method, whereby the patient must possess the necessary strength, dexterity, and cognitive capacity to provide a clean urine sample under the direction of a healthcare professional. However, the "clean catch" method is rarely ever clean. This method requires the patient to wash her hands, balance herself in a squatting position over the toilet or commode while spreading her labia with her fingers and wiping the vulva and perineum from front to back three times using three separate antiseptic wipes, initiate a urine stream into the toilet, collect the mid-stream portion of her urine into a specimen cup without contaminating the cup with her fingers or spilling the contents all over herself or the floor, and screw the lid onto the specimen cup so that it does not leak. The result is a high rate of contaminated urine samples and agitated patients. The second method for collecting a urine specimen for urinalysis is the "straight cath" method, whereby urine is drained from the patient's bladder by inserting a straight catheter into the urethra after wiping the genitals with iodine or some other irritating antiseptic. The latter method is invasive, uncomfortable for the patient, and requires specialized equipment. Moreover, the process of inserting anything into the urethra can cause urinary tract infections.

Traditional non-invasive and non-sterile female urine drainage devices include bedpans and funnels. However, urine samples collected using bedpans are contaminated and unsuitable specimens for urinalysis. Moreover, bedpans are awkward, uncomfortable, difficult to use, and prone to spillage. There also exist cones and funnels for use by female subjects in a standing position. These are generally marketed for use in public restrooms or outdoor environments and are not known to be used in the clinical setting.

The various barriers described above reveal the need for a better methods for both emptying the bladder and collecting a clean urine sample from female patients. This is especially true for those experiencing barriers to mobility and/or cognition. Specifically, there exists a need for a device that can collect a clean urine specimen without the use of catheterization. Such a device should not be overly complicated and should be easy to use in a clinical setting. The patient should be able to use the device from multiple angles and positions according to the limitations imposed by the clinical condition. It may also be used outside traditional healthcare settings where sufficient access to toilets are limited, due either to scarcity of facilities or barriers to mobility.

SUMMARY

The present disclosure relates to an improved urine collection device configured to enable a female to provide a clean urine sample and empty the bladder from multiple angles and positions. The patient may be in a supine, prone, right or left lateral recumbent, Fowler's, reverse Trendelenburg, Sims, lithotomy, knee-chest, jackknife position, or any variation thereof.

The urine collection and drainage device can comprise a device body comprising a vulva-facing portion and a handle portion. The device body can further comprise an anterior end and a posterior end. The vulva-facing portion can comprise a bulbous protuberance at the posterior end and a partial dome portion in proximity to the anterior end. The size and shape of the device can vary slightly to accommodate the size and shape of the patient. For example, the pediatric version will be smaller and possibly more curved where it meets the vulva vestibule, and the bariatric version will be larger and less curved where it meets the vulva vestibule. The superior aspect of this device is designed to fit snugly against the vulva vestibule whereby it is surrounded by the labia minora on all sides to create a water-tight seal around the edges of urethral opening, creating an open channel for urine to freely flow into a receptacle uncontaminated by the flora of the surrounding anatomical structures.

The bulbous protuberance and the posterior ridge can be configured to be used to spread apart a labia minora of a subject to expose a urethral-opening of the subject while mechanically pushing bacteria away from the urethral opening, depending on the surface texture of the device. The bulbous protuberance can be configured to rest against at least part of a vaginal opening of the subject while either the posterior ridge or bulbous protuberance rests against the fourchette and the urine collection slot surrounds the urethral-opening. The dome portion can be configured to rest against the anterior portion of the vulva vestibule and surrounded by the labia minora when the urine collection slot surrounds the urethral-opening. The partial dome portion can be positioned superior or above the bulbous protuberance when the patient is in a supine position. The partial dome portion can be positioned anterior to the bulbous protuberance when the patient is in a standing position. The bulbous protuberance can have a protuberance width between about 0.5 cm and about 4 cm.

The handle portion can further comprise a base protuberance positioned at the anterior end and inferior or below the partial dome portion. The handle portion can further comprise a contoured handle groove defined along both handle lateral sides. The contoured handle groove can be positioned inferior or below the partial dome portion.

The urine collection and drainage device can further comprise a urine collection slot defined along a urethra-facing side of the vulva-facing portion in between the bulbous protuberance and the partial dome portion. The urine collection slot can be in fluid communication with the drainage opening through an interior cavity defined within the device body. The urine collection slot can be bounded by a first sloped lateral surface and a second sloped lateral surface. The first sloped lateral surface and the second sloped lateral surface can converge toward one another as the first sloped lateral surface and the second sloped lateral surface approach the urine collection slot. The urine collection and drainage device can further comprise a drainage opening defined along a base of the device body.

The urine collection slot can be curved when viewed from the side of the device. The urine collection slot can have a slot width. The slot width can be between about 0.25 cm and about 1.0 cm. The urine collection slot can have a slot length. The slot length can be between about 1.0 cm and about 5.0 cm. A ratio of the slot length to the slot width can be between about 3:1 to about 10:1.

The urethra-facing side can be curved when viewed from a side of the device. The urethra-facing side can have a radius of curvature of between about 8.0 cm and about 12.0 cm. The device body can have a minimum device height as measured from the base of the device body to a low point along the urethra-facing side. The minimum device height can be 4.0 cm. The device body can have a maximum device width of between about 3.0 cm and 5.0 cm. The device body can have a maximum body length. The body length can be between about 7.5 cm to about 12.5 cm.

The device can further comprise a urine collection bag or a urine collection receptacle coupled to at least part of an interior cavity wall of the device body. The urine collection bag or the urine collection receptacle extends through the drainage opening and can be configured to receive a clean urine sample.

A method of collecting a clean urine sample from a subject is also described herein. The method can comprise providing a urine collection device comprising a device body having a vulva-facing portion and a handle portion. The vulva-facing portion can comprise a bulbous protuberance atop a posterior ridge at a posterior end of the device body and a partial dome portion in proximity to an anterior end of the device body. A urine collection slot can be defined along a urethra-facing side of the vulva-facing portion in between the bulbous protuberance and the partial dome portion. The method can further comprise positioning the urine collection device such that the urine collection slot surrounds a urethral-opening of the subject, the bulbous protuberance rests against at least part of a vaginal opening of the subject, the posterior ridge rests against the fourchette, and the partial dome portion rests against the anterior portion of the vulva vestibule and is surrounded by the anterior portion of the labia minora of the subject. The method can further comprise allowing urine to be collected through the urine collection slot. The method can further comprise using the bulbous protuberance and/or the posterior ridge to spread apart a labia minora of a subject to expose the urethral-opening of the subject.

In another variation, a method of collecting a clean urine sample from a subject can comprise holding a urine collection device using one hand by placing a base protuberance of a handle portion of the urine collection device in contact with or against a palm of the one hand and grasping a contoured handle groove defined along lateral sides of the handle portion with a plurality of fingers of the one hand. The urine collection device can further comprise a device body having an anterior end, a posterior end having a posterior ridge defined thereon, and a vulva-facing portion. A urine collection slot can be defined along a urethra-facing side of the vulva-facing portion in between the anterior end and the posterior end. The method can further comprise using the posterior end of the urine collection device to spread apart a labia minora of a subject to expose a urethral-opening of the subject. The method can further comprise holding the urine collection device in place when the urine collection slot surrounds the urethral-opening of the subject. The method can further comprise allowing urine to be collected through the urine collection slot. The method can further comprise using at least one of the posterior ridge and a bulbous protuberance defined atop of the posterior ridge to spread apart a labia minora of a subject to expose the urethral-opening of the subject.

DETAILED DESCRIPTION

Disclosed is an improved urine collection and drainage device 100 for female patients. The device 100 can be used on subjects who experience barriers to voiding in a standard toilet. One possible setting is healthcare. For example, the device 100 can be used to drain the bladder or collect a clean urine specimen from a female who is bedbound, chairbound, or unable to change positions safely or easily due to her clinical condition. The device 100 can also be referred to as a urine catchment device.

The device 100 can be made of a polymeric material, a metallic material, a ceramic material, or a composite or combination thereof. For example, the device 100 can be made in whole or in part of a biocompatible polymeric material such as medical grade polyvinyl chloride (PVC), high-density polyethylene (HDPE), polyethylene terephthalate glycol (PETG), polycarbonate (PC), polypropylene (PP), polyurethane (PU), polyethylenimine (PEI), polysulfone, silicone, or a combination or copolymers thereof. The device 100 can also be made in part or in whole of a metallic material such as aluminum or stainless steel. The device 100 can also be made in part or in whole of a ceramic or porcelain material. In some variations, the device 100 can be made of an inexpensive single-use material, a recyclable material, or a biodegradable material approved for use in a healthcare setting.

Figure 1A:
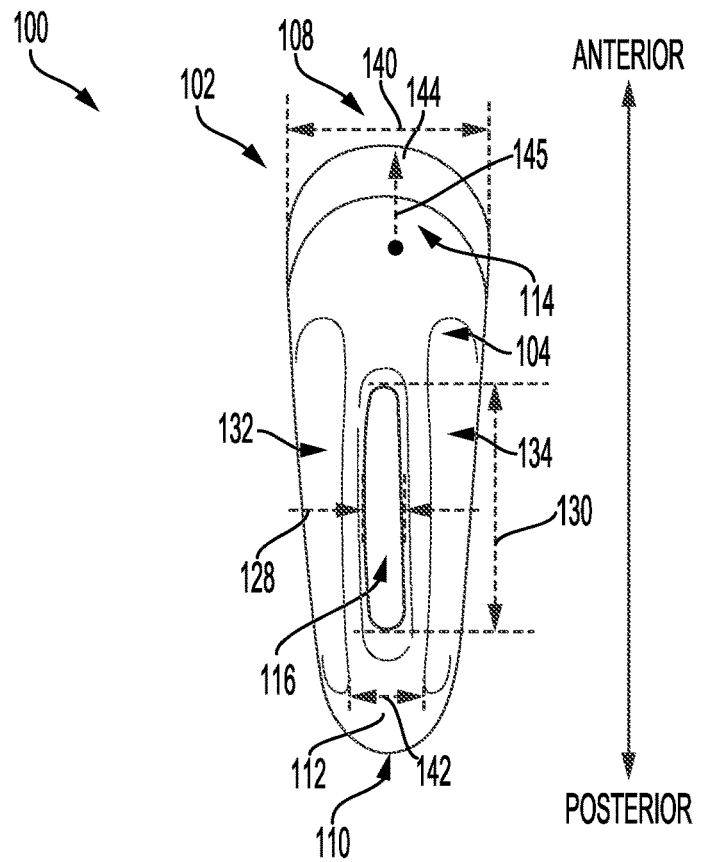
FIG. 1A illustrates a top plan view of a variation of the urine collection and drainage device.

FIG. 1A illustrates a top plan view of a variation of the urine collection and drainage device 100. The urine collection and drainage device 100 can have a device body 102 comprising a vulva-facing portion 104 and a handle portion 106. The device body 102 can comprise an anterior end 108 and a posterior end 110, both of which can be rounded. The vulva-facing portion 104 and the handle portion 106 can converge to form the anterior end 108 and a posterior end 110 at opposite ends of the device 100. The vulva-facing portion 104 can be curved or concave and configured to contact the anatomy of a patient.

The vulva-facing portion 104 can comprise a urine collection slot 116, a first lateral surface 132, and a second lateral surface 134. The urine collection slot can be defined along a urethra-facing side 118 of the vulva-facing portion 104 between the anterior end 108 and the posterior end 110. The urethra-facing side 118 can be curved when viewed from a side of the device 100.

Figure 1B:
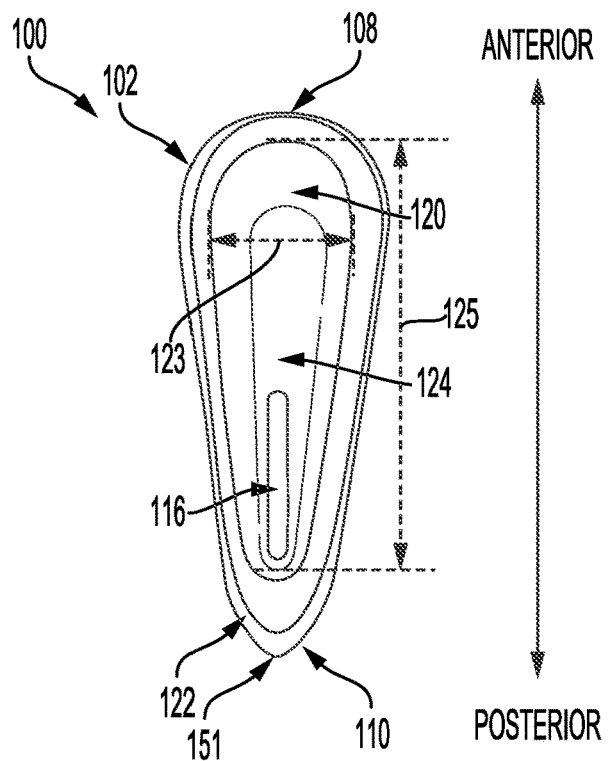
FIG. 1B illustrates a bottom plan view of the urine collection and drainage device.

The urine collection slot 116 can be defined along the urethra-facing side 118 of the vulva-facing portion 104 in between the bulbous protuberance 112 and the partial dome portion 114. The urine collection slot 116 can be a curved elongated slot or slit opening through which urine can pass through and can extend through the device 100 from the vulva-facing portion 104 to the handle portion 106. As illustrated in FIG. 1B, the urine collection slot 116 can extend to a drainage opening 120 and the interior cavity 124 of the device 100 for the collection of urine.

The urine collection slot 116 can be curved when viewed from the side of the device 100. The urine collection slot can have a slot width 128. The slot width 128 can be between about 0.50 cm and about 1.0 cm. The urine collection slot can have a slot length 130. The slot length 130 can be between about 3.0 cm and about 5.0 cm. A ratio of the slot length 130 to the slot width 128 can be between about 3:1 to about 10:1.

The urine collection slot 116 can be bounded by a first sloped lateral surface 132 and a second sloped lateral surface 134. The first lateral surface 132 and the second lateral surface 134 can converge toward one another as the first lateral surface 132 and the second lateral surface 134 approach the urine collection slot 116. The first lateral surface 132 and the second lateral surface 134 can be curved and sloped. The sloped and curved contour of the first lateral surface 132 and the second lateral surface 134 can allow the surfaces to accommodate the anatomy of a female patient.

For example, when the device 100 is placed into position against the female patient, the labia minora of the patient can surround the first lateral surface 132 and the second lateral surface 134 or fit snuggly around at least part of the labia minora. The vulva-facing side can fit snugly against the vulva vestibule. The design of the device 100 can allow a clean urine sample to be collected through the device 100 without the patient worrying about leakage.

The urine collection and drainage device 100 can further comprise a drainage opening 120 defined along a base 122 of the device body 102. The drainage opening 120 can extend from a bottom of the handle portion 106. The drainage opening 120 can have a port outer diameter ranging from about 1.0 cm to 3.0 cm (e.g., about 2.0 cm).

The urine collection slot 116 can be in fluid communication with the drainage opening 120 through an interior cavity 124 defined within the device body 102. For example, urine entering through the urine collection slot 116 can flow through the interior cavity 124 and out through the drainage opening 120 into a specimen cup or drainage bag without becoming contaminated by the microbial flora of the surrounding skin or vaginal area. This is important when urine is collected from a female patient for further analysis or diagnostic purposes.

The vulva-facing portion 104 can comprise a bulbous protuberance 112 at a posterior end 110 and a partial dome portion 114 in proximity to the anterior end 108. The urine collection slot 116 can be defined in between the bulbous protuberance 112 and the partial dome portion 114. The bulbous protuberance 112 can be configured to be used as a wedge to spread apart a labia minora of a subject to expose a urethral-opening of the subject. This can be useful when either the subject or a healthcare professional is handling the device 100 with one hand.

The bulbous protuberance 112 can be configured to rest against at least part of a vaginal opening of the subject when the urine collection slot 116 surrounds the urethral-opening. The bulbous protuberance 112 can be sized to partially block or obstruct the vaginal opening. In some variations, at least part of the bulbous protuberance 112 can extend into the vaginal opening while the posterior ridge 151 fits snugly into the lowest point of the fourchette and the urine collection slot 116 surrounds the urethra of the subject.

The bulbous protuberance 112 can have a protuberance width 142 between about 1.0 cm to about 2.0 cm (e.g., about 1.5 cm). The bulbous protuberance 112 can have a protuberance radius extending from the vulva-facing portion 104. The protuberance radius can be range from about 0.5 cm to about 1.5 cm (e.g., about 1.0 cm). When the bulbous protuberance 112 is substantially dome-shaped, the protuberance width 142 can be considered a diameter of the bulbous protuberance 112.

The partial dome portion 114 can be positioned in proximity to or near the anterior end 108 but not at the anterior end 108. The partial dome portion 114 can be configured to rest snugly against the vulva vestibule at the anterior end 108 of the device 100, while the surrounding edges of the partial dome portion 114 rest against the labia minora of the subject when the urine collection slot 116 surrounds the urethral-opening.

The partial dome portion 114 can be positioned inferior or below the bulbous protuberance 112 and superior or above the base protuberance 144 (see, e.g., FIGS. 1E ad 1F). As understood by one of ordinary skill in the art, superior/inferior in this context refers to the relative positioning of the aforementioned components of the device when viewing the device body 102 from the side (when the device 100 is not in use and when the device base 122 is placed on a flat surface).

The posterior ridge 151 can have a ridge height, the ridge height can be between about 1.0 cm to about 8.0 cm. For example, the ridge height can be about 4.0 cm.

FIG. 1B illustrates a bottom plan view of the urine collection and drainage device 100. The handle portion 106 can comprise a relatively flat base 122 on the back of the device 100. The handle portion 106 can have a drainage opening 120 for allowing urine to pass out of the internal cavity 124 of the device body 102 and into a collection bag, cup, or another type of container. The drainage opening 120 can be in fluid communication with the urine collection slot 116 via the interior cavity 124 (i.e., the hollow interior of the device body 102). The interior cavity 124 can have a cavity length 125 ranging from about 5.0 cm to about 10.0 cm (e.g., about 7.5 cm). The interior cavity 124 can be tapered along the length of the device 100. The interior cavity 124 can also have a maximum cavity width 123. The maximum cavity width 123 can range from about 1.0 cm to about 3.0 cm (e.g., about 2.0 cm) and can taper towards the posterior end 110.

The handle portion 106 can further comprise a base protuberance 144 positioned at the anterior end 108 and inferior or below the partial dome portion 114. The base protuberance 144 positioned on the handle portion 106 can have a base protuberance radius of curvature 145 ranging from about 1.0 cm to about 3.0 cm (e.g., about 2.0 cm).

Figure 1C:
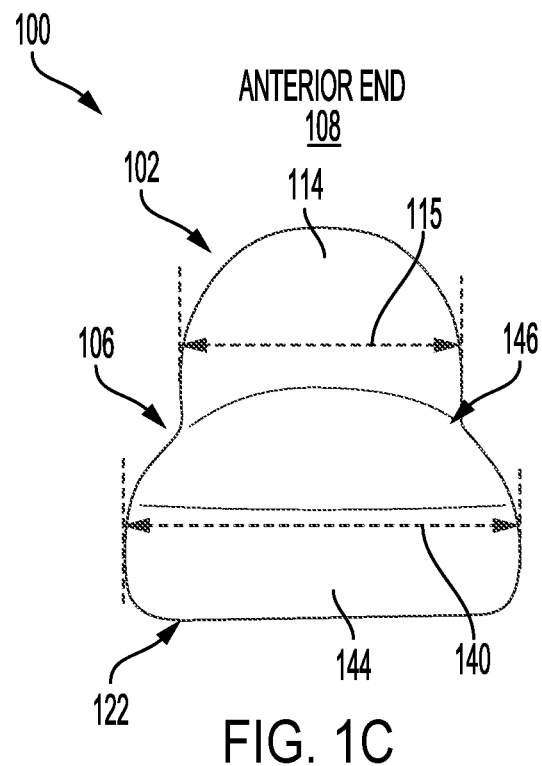
FIG. 1C illustrates an anterior end of the urine collection and drainage device.

FIG. 1C illustrates the anterior end 108 of the urine collection and drainage device 100. As shown in FIG. 1C, a dome width 115 of the partial dome portion 114 can be greater than a base width 140 of the base protuberance 144. For example, the dome width 115 can range from about 2.0 cm to about 4.0 cm (e.g., about 3.0 cm) and base width 140 can range from about 3.0 cm to about 5.0 cm (e.g., about 4.0 cm).

FIG. 1C also illustrates that all edges and ends of the device 100 can be rounded and smoothed to prevent any part of the device 100 from causing injury to delicate tissues when the device 100 is being maneuvered into position.

Figure 1D:
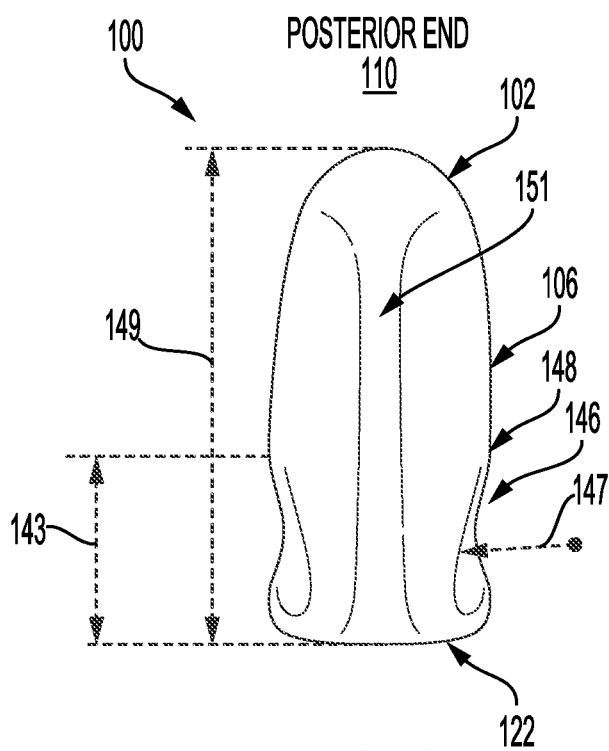
FIG. 1D illustrates a posterior end of the urine collection and drainage device.

FIG. 1D illustrates the posterior end 110 of the urine collection and drainage device 100. The device 100 can have a maximum body height 149 ranging from about 4.0 cm to about 6.0 cm (e.g., about 5.0 cm).

The handle portion 106 can further comprise a contoured handle groove 146 defined along both of the handle lateral sides 148. The contoured handle groove 146 can be positioned inferior or below the partial dome portion 114. The contoured handle groove 146 can extend circumferentially around a perimeter of the handle portion 106. The contoured handle groove 146 can be curved or sloped. The contoured handle groove 146 can serve as a channel or receiving surface for the fingers of the user when the user holds the device 100 when maneuvering the device 100 into position and when the user collects voided urine from the subject. There can also be an exterior groove defined around the exterior surface of the device 100 in proximity to the device base 122 with which to hold a urine collection bag 300 in place with a rubber band.

The contoured handle groove 146 can have a groove height 143 extending from the device base 122 to the top of the contoured handle groove 146. The groove height 143 can range from about 1.0 cm to about 3.0 cm (e.g., about 2.0 cm). The contoured handle groove 146 can have a groove radius of curvature 147. The groove radius of curvature 147 can range from about 2.0 cm to about 4.0 cm (e.g., about 3.0 cm).

Figure 1E:
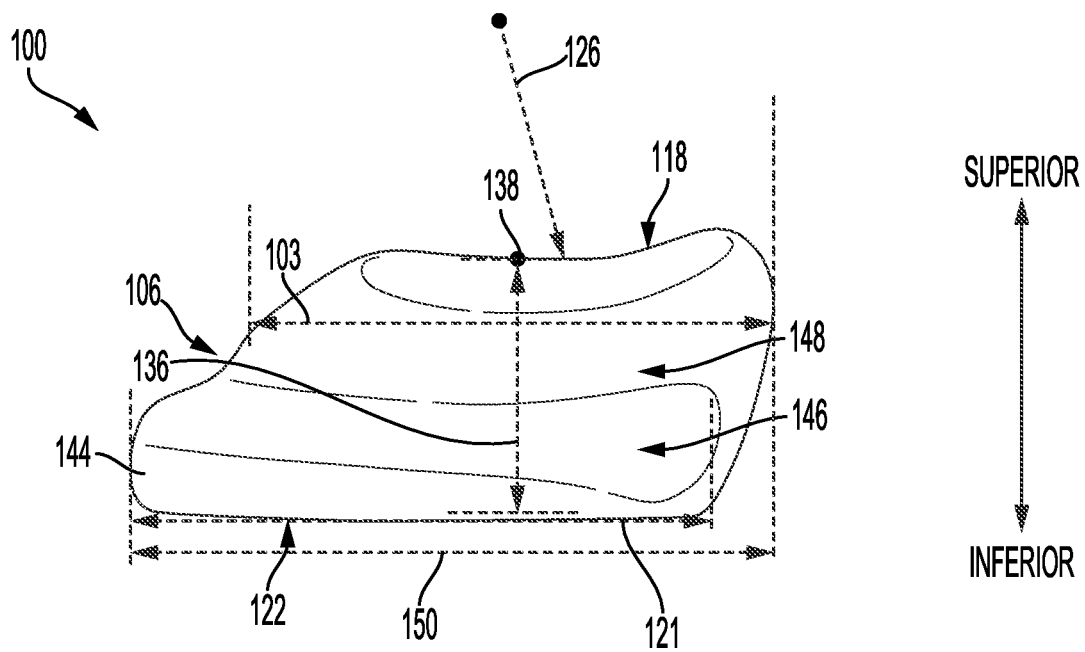
FIG. 1E illustrates a side view of the urine collection and drainage device.
Figure 1F:
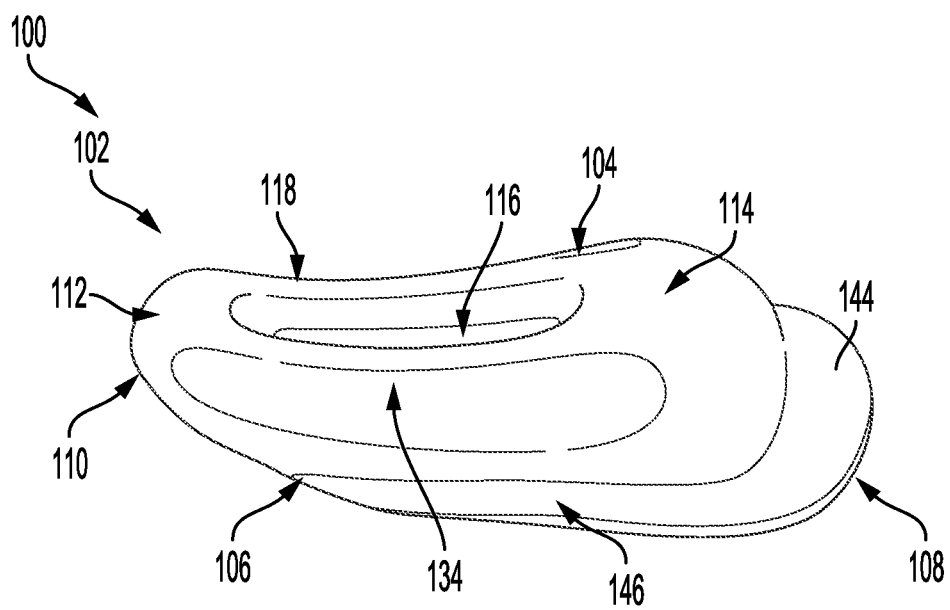
FIG. 1F illustrates a top perspective view of the urine collection and drainage device.

FIGS. 1E and 1F illustrate side and top perspective views of the urine collection and drainage device 100, respectively. The device 100 can have an entire body length 150 ranging from about 9.5 cm to about 12.5 cm (e.g., about 10.0 cm). The device 100 can also have a vulva-facing portion length 103 and a base length 121. The base length 121 can be greater than or equal to the vulva-facing portion length 103. In some variations, both the base length 121 and the vulva-facing portion length 103 can be less than the entire body length 150.

The vulva-facing portion length 103 can range from about 7.5 cm to about 9.0 cm (e.g., about 8.5 cm). The base length 121 can range from about 7.5 cm to about 9.0 cm (e.g., about 9.0 cm).

The device body 102 can have a minimum device height 136 as measured from the base 122 of the device body 102 to a low point 138 along the urethra-facing side 118. The minimum device height 136 can be about 4.0 cm. In some variations, the device body 102 can have a maximum device width of about 5.0 cm.

As shown in FIG. 1E, the urethra-facing side 118 can be curved when viewed from a side of the device 100. The urethra-facing side 118 can have a radius of curvature 126 of between about 8.0 cm to about 12.0 cm (e.g., about 10.0 cm).

Figure 1G:
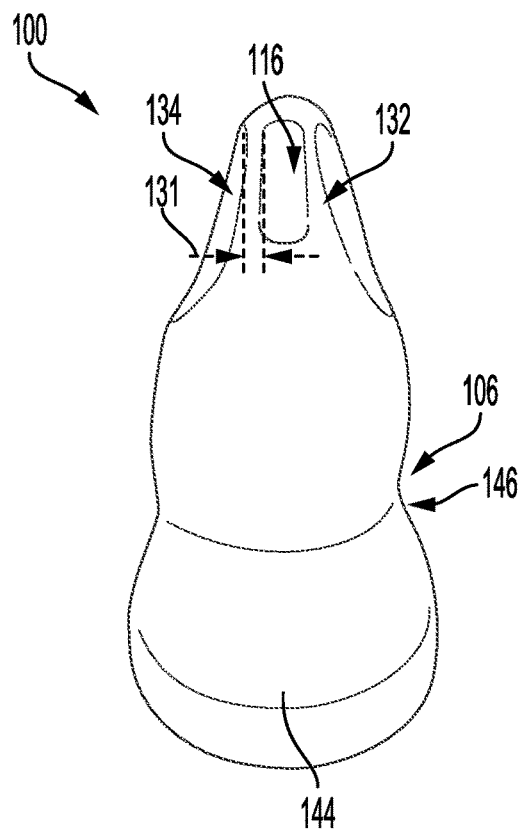
FIGS. 1G and 1H illustrate angled views of the urine collection and drainage device.
Figure 1H:
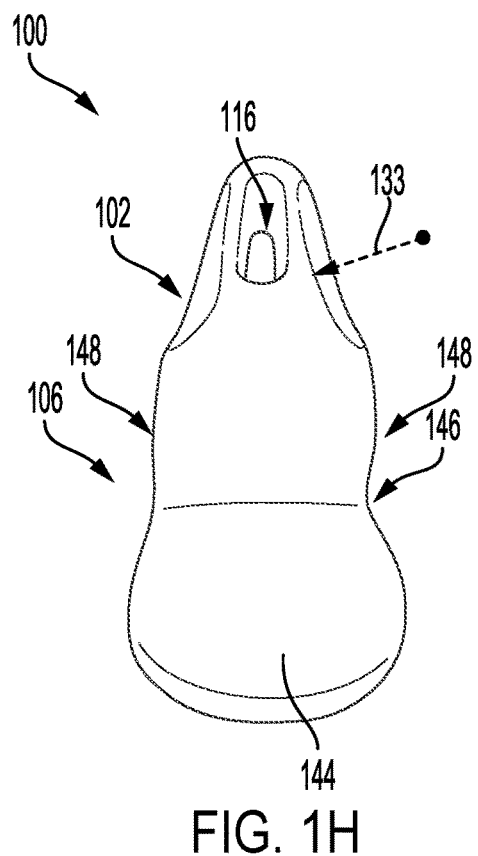

FIGS. 1G and 1H illustrate angled views of the urine collection and drainage device 100. As shown in FIG. 1G, a top or superior portion of the first sloped lateral surface 132 and the second sloped lateral surface 134 can serve as slot walls defining the urine collection slot 116. Each of the slot walls can have a slot wall thickness 131. The slot wall thickness can range from about 0.2 cm to about 0.8 cm (e.g., about 0.5 cm).

FIG. 1H illustrates that the first sloped lateral surface 132 and the second sloped lateral surfaces 134 can each have a surface radius of curvature 133. The surface radius of curvature 133 can range from about 3.0 cm to about 5.0 cm (e.g., about 4.0 cm).

Figure 2A:
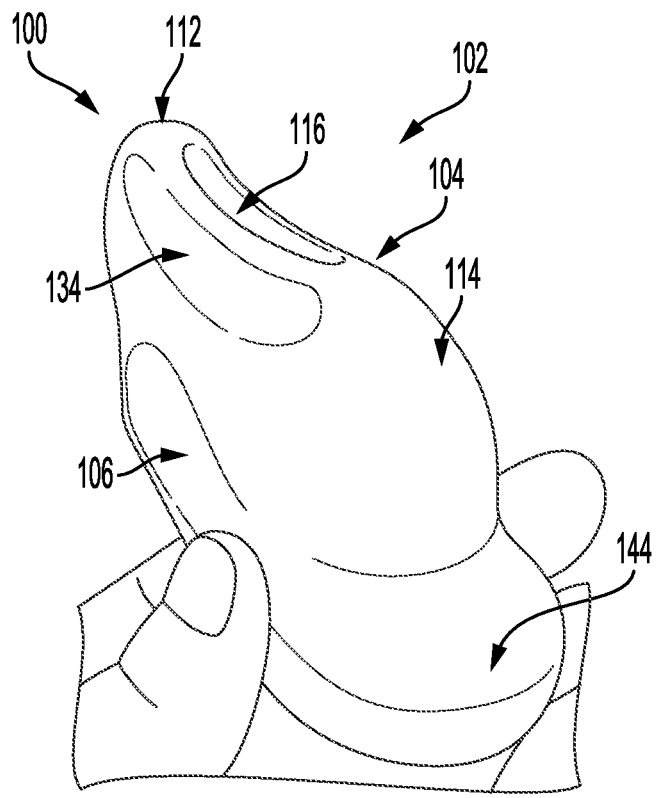
FIGS. 2A and 2B illustrate perspective views of the urine collection and drainage device being held by a user.
Figure 2B:
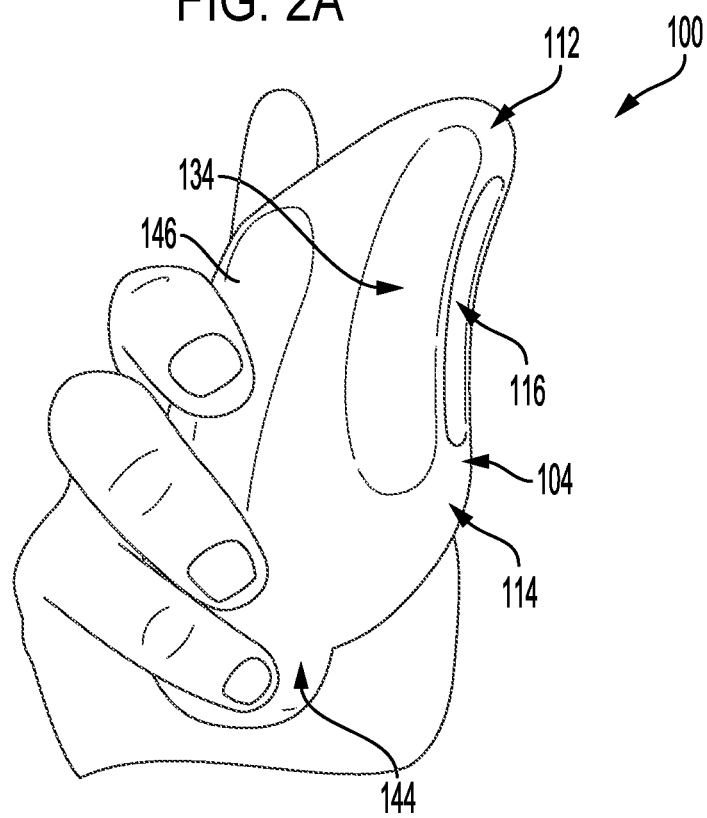

FIGS. 2A and 2B illustrate perspective views of a variation of the urine collection and drainage device 100 being held by a user. The ergonomics of the device 100 can allow the user to hold the device in various ways with only one hand. This can be especially useful when the patient is in a supine position. For example, FIG. 2A illustrates the user holding the handle portion 106 of the device 100 toward the anterior end 108 or near the base protuberance 144 with a thumb and index finger of the user. Moreover, FIG. 2B illustrates the user holding the device in one hand such that the base protuberance 144 rests against the user's palm and the user's middle, ring, and pinky fingers curl around the contoured handle groove 146 on one lateral side 148 of the handle portion 106 while the user's thumb holds the contoured handle groove 146 on the other lateral side 148 of the handle portion 106. This way of holding the device 100 can be helpful in allowing the user to maneuver the device 100 into position while the patient is laying down, sitting, or standing.

One technical problem faced by the applicant is how to design a handheld urine collection device where the hand or fingers of the user holding the device does not contaminate the urine sample being collected. One technical solution discovered and developed by the applicant is to design the device 100 to have a large protruding base protuberance 144 at an anterior end 108 of the device positioned inferior to a contoured handle groove 146 defined along both lateral sides 148 of the device 100. When the device 100 is designed in this manner, a user naturally/instinctively holds the handle portion 106 of the device 100 in ways that keep the fingers of the user away from the vulva-facing portion 104 of the device 100 including the urine collection slot 116 (thereby mitigating the risk of sample contamination by the user's fingers). The watertight seal created by the device 100 prevents the urine from coming into fluid contact with the vagina, labia, and surrounding skin. A urine collection bag 300 attached to the device 100 (see, e.g., FIG. 3) can also act as a barrier to prevent the urine from fluidly contacting the fingers of the user. The device 100 can be held in place by contact with the posterior ridge 151 with the fourchette of the female user.

Another technical problem faced by the applicant is how to access the patient's urethra without having to maneuver the patient into a position where the urethra can be clearly isolated and visualized, as is the case for urinary catheterization. The solution lies in the way the device 100 can slide into place from the anterior aspect of the vulva and spreads the labia while it is inserted posteriorly and stops at the fourchette, indicating it is in the proper position. This device 100 can be easily slid into position from multiple angles and positions. This extremely useful feature sets this device apart from any other female urinary device currently on the market.

Another technical problem faced by the applicant is how to design a urine catchment device for females to use while lying in a supine position, since the forces of gravity interfere with the functioning of other devices such as funnels and female urinals. These devices are generally designed to be placed on the vulva outside the labia and leave an open channel for leakage. One technical solution discovered and developed by the applicant is to design the device 100 to have a shape that corresponds closely with the vulva vestibule so that the shape of the labia minora serves to form a seal around the device, preventing it from leaking. The downward pressure of the posterior ridge of the device against the fourchette further helps to confirm proper placement and to form a closer seal.

Another technical problem faced by the applicant is how to design a urine catchment device that can be easily used by both the caregiver and the patient herself, allowing for increased patient autonomy. The solution lies in the shape of the handle and corresponding ridges which allow for the hand and fingers to fit comfortably around the device from multiple angles so that it can be positioned from multiple angles.

Another technical problem faced by the applicant is how to design a urine catchment device that fits closely with the anatomy of a wide range of varying body shapes and sizes. The solution lies in the rounded shape and gently-sloping curvature that will accommodate variations in anatomy.

Another technical problem faced by the applicant is how to design a urine catchment device that minimizes splashback by allowing urine to flow freely into a receptacle (e.g., a urine collection bag 300) without needing to overcome the forces of gravity and the narrowed circumference of a drainage channel, as is the shortcoming of standard female urine funnels today. The solution lies in the snug seal against the body and the tapered cone-like shape of the interior cavity 124 of the device 100, as opposed to the standard funnel shape of typical female urinary devices.

Moreover, FIG. 2A illustrates that the first and second lateral surfaces 132, 134 can each have respective curved lateral surface first and second ends. The lateral surface first end, which is positioned towards the anterior end 108, can have a larger radius or indent than the lateral surface second end, which is positioned towards the posterior end 110.

Figure 3:
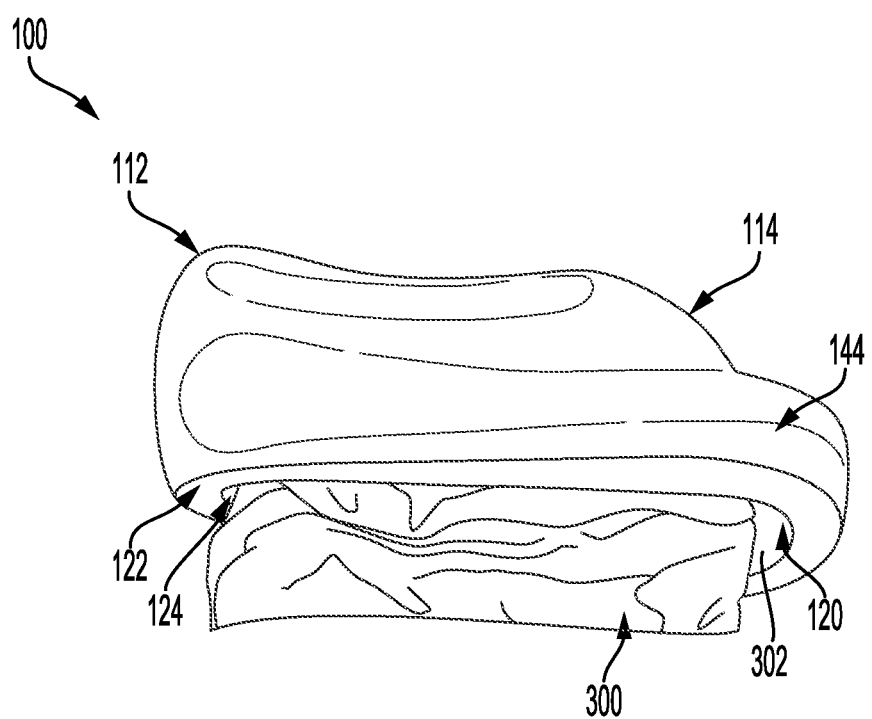
FIG. 3 illustrates a side view of a variation of the urine collection and drainage device having a urine collection bag coupled thereto.

FIG. 3 illustrates a side view of a variation of the urine collection and drainage device 100 having a urine collection bag 300 coupled thereto. The urine collection bag 300 or, alternatively, a urine collection receptacle can be coupled to an inside of the interior cavity 124 at the handle portion 106. For example, the urine collection bag 300 or the urine collection receptacle can be coupled or otherwise affixed to at least part of an interior cavity wall 302 of the device body 102. An adhesive can be used to adhere the urine collection bag 300 to the interior cavity wall 302 of the device body 102. When a urine collection receptacle is used instead of a urine collection bag 300, the urine collection receptacle can be coupled to the device body 102 via a mating feature, a snap fit, or an interference fit. The urine collection bag 300 or the urine collection receptacle can extend through the drainage opening 120 and can be configured to receive a clean urine sample.

The urine collection bag 300 can have a pre-perforated segment or section defined along or near a superior end of the urine collection bag 300 (i.e., the end adhered to the interior cavity wall 302 of the device body 102) such that one part of the urine collection bag 300 (the part containing the clean urine sample) can be detached or ripped away from another part of the urine collection bag 300 (the part adhered to the interior cavity wall 302 of the device body 102). The urine collection bag 300 can also be self-sealing such that the part of the urine collection bag 300 containing the clean urine sample is sealed onto itself once that part of the urine collection bag 300 is detached or ripped away from the remainder of the urine collection bag 300 still adhered to the device body 102. A detachable and self-sealing urine collection bag 300 can allow a user (e.g., a healthcare professional or the patient) to cleanly remove the urine collection bag 300 from the device 100 and transport the urine collection bag 300 for analysis.

Alternatively, the drainage opening 120 can be shaped and sized to receive a barbed adapter of a drainage tube extending from the urine collection bag 300. The drainage tube can also be coupled to or extend into a commode, a specimen cup, a bedpan, or a toilet. In other variations, the drainage opening 120 can be coupled directly to or fit into a specimen cup.

A method of using the urine collection and drainage device 100 is also disclosed. The method can comprise a healthcare professional (e.g., a nurse/caregiver) or the patient herself cleaning the vulva and using the bulbous protuberance 112 (and/or the posterior ridge 151) to spread apart the labia minora of the patient. The method can also comprise sliding at least part of the device 100 (e.g., the vulva-facing portion 104) between the labia minora of the patient until the urine collection slot 116 surrounds a urethral opening of the patient. The method can further comprise resting a bulbous protuberance 112 of the device 100 against a vaginal opening and the posterior ridge 151 resting against the fourchette of the patient when the urine collection slot 116 surrounds the urethral opening of the patient. The bulbous protuberance 112 can be positioned at a posterior end 110 of the vulva-facing portion 104. The method can further comprise collecting the patient's voided urine through the urine collection slot 116. The urine collection slot 116 can be in fluid communication with the drainage opening 120 through the interior cavity 124 defined within the device 100.

Figure 4A:
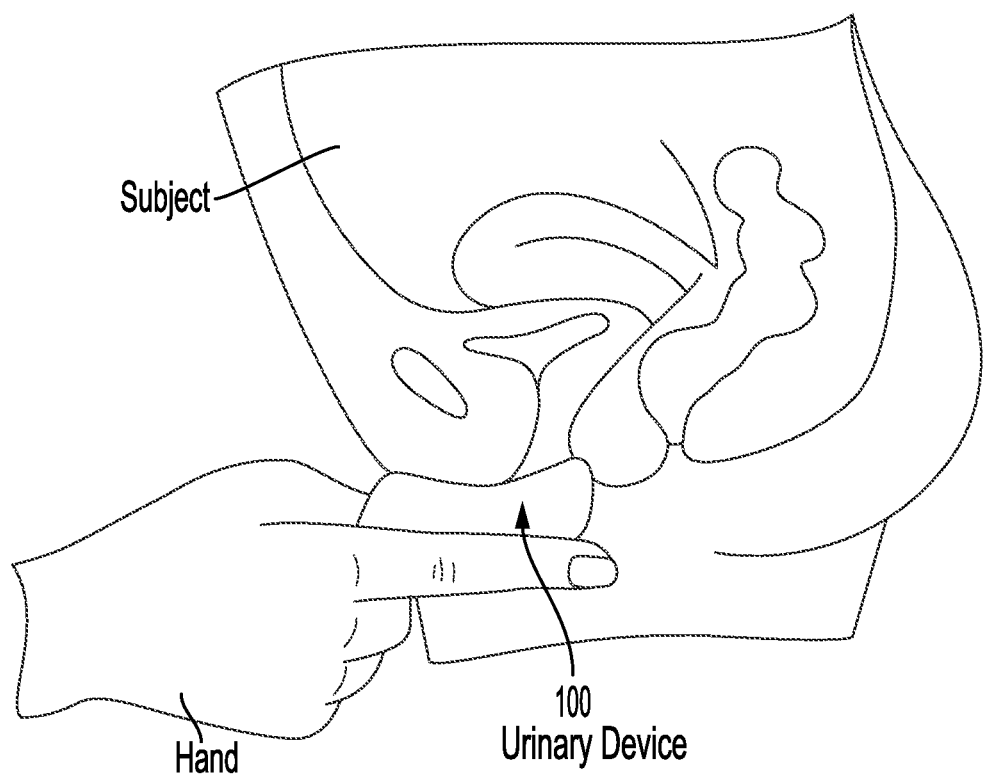
FIG. 4A illustrates the urine collection and drainage device being held by one hand and used on a subject.

FIG. 4A illustrates the urine collection and drainage device 100 being held by one hand of a healthcare professional or the patient herself. To deliver the device 100, the device 100 can be held with one hand by either a user or the patient herself. The handle portion 106 of the device can be grasped via the contoured handle groove 146 such that the user can avoid touching the vulva-facing portion 104 of the device 100, limiting contamination of the device 100. As discussed above, the user can use the bulbous protuberance 112 to spread open the labia minora. The partial dome portion 114 of the device 100 can eventually rest against the vaginal vestibule where it is surrounded by the labia minora while the bulbous protuberance 112 can rest near the vagina and the posterior ridge 151 can rest against the fourchette. When maneuvered into position for urine collection, the anterior end 108 of the device 100 can be positioned superior to the urethral opening while the posterior end 110 can be positioned inferior to the urethral opening. The patient can then pass urine through the urine collection slot 116, into the interior cavity 124 of the device 100, and out through the drainage opening 120 into a urine collection bag 300 (see, e.g., FIG. 3), a commode, a specimen cup, a drainage bag, or a urine collection receptacle. The device 100 can be used for patients that can relax their pelvic floor muscles and void on command.

When maneuvered into position for urine collection, the device 100 can be held in place by the patient's right inner thigh resting against the right lateral side of the device 100 and the patient's left inner thigh resting against the left lateral side of the device 100. This can be done in lieu of or in addition to the user holding the device 100 with the user's fingers.

Figure 4B:
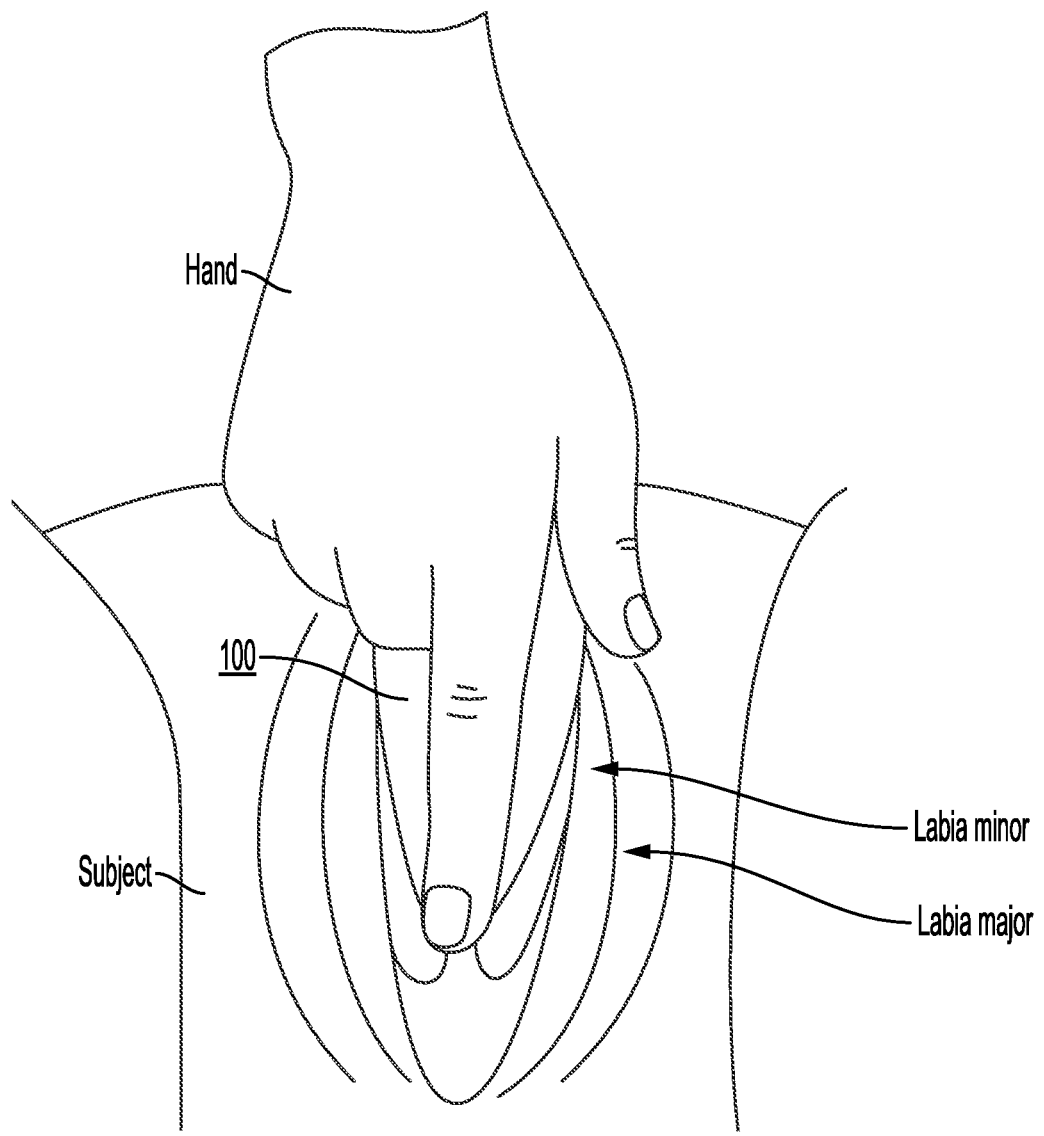
FIG. 4B illustrates the urine collection and drainage device being held by one hand and moved into position to collect urine from a subject.

FIG. 4B illustrates the urine collection and drainage device 100 being held by one hand and moved into position to collect urine from a subject. The user (e.g., the subject or a healthcare professional) can guide the base 122 of the device 100 with the user's index finger during placement. When the patient is guiding the device 100 into position, this can allow the patient the ability to potentially feel the device 100 spreading the patient's labia. When a healthcare professional is guiding the device 100 into position, this can allow the healthcare professional the ability to visualize or see the device 100 relative to the patient's anatomy.

One advantage of the urine collection and drainage device 100 is that the device 100 can reduce the likelihood that urine samples will be contaminated during the collection process. Another advantage of the urine collection and drainage device 100 is that the device 100 can simplify the process of acquiring urine samples from a female patient (especially when the patient is unable to use the toilet). Another advantage of the urine collection and drainage device 100 is that the device can decrease the need for bedpans. Another advantage of the urine collection and drainage device 100 is that the device can decrease the incidence of injury to patients and caregivers because it requires a minimal amount of maneuvering to use. Yet another advantage of the urine collection and drainage device 100 is that the device 100 can decrease the need for painful urethral catheterization. A further advantage of the urine collection and drainage device 100 is that the device 100 can allow a female patient to easily drain their bladders while immobile in bed. Moreover, the design of the urine collection and drainage device allows patients to use it independently and discreetly, allowing for increased autonomy and dignity.

Figure 5:
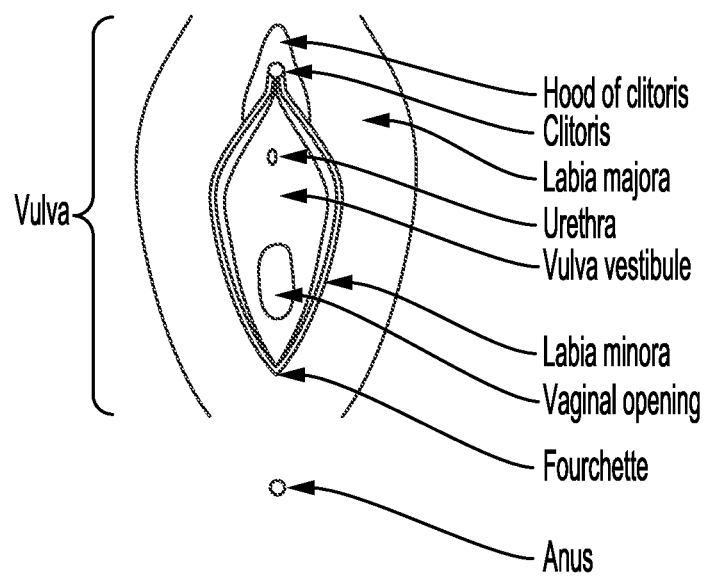
FIG. 5 is a schematic diagram of the relevant anatomical structures of the female vulva for illustrative purposes.

FIG. 5 is a schematic diagram of the relevant anatomical structures of the female vulva for illustrative purposes. The diagram shows a frontal view of the female vulva. As described above, the bulbous protuberance 112 and/or the posterior ridge 151 can be used to spread open the labia minora to position the device 100 within a female patient. In some variations, the device 100 can be positioned partly within the patient to obtain a clean urine sample from the patient because the device 100 fits snugly against the vaginal vestibule, forming a barrier between the urethra and the surrounding anatomical structures. For example, the bulbous protuberance 112 can rest against the vaginal opening of the subject and the partial dome portion 114 can rest against the vaginal vestibule and the labia minora, or a combination thereof to when the urine collection slot 116 is aligned with the urethra opening of the patient.

Figure 6A:
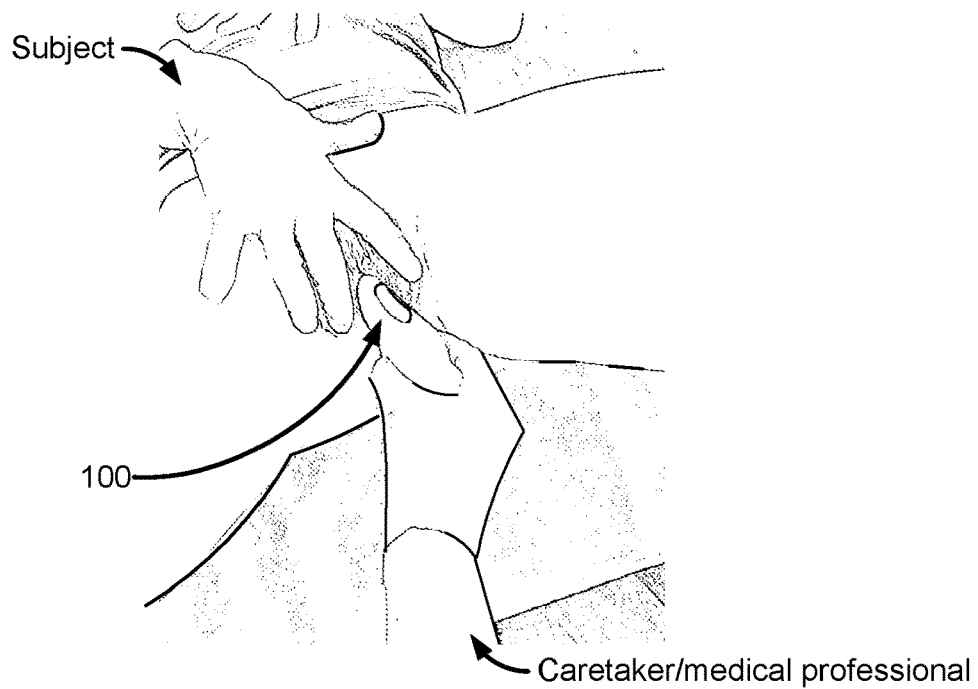
FIGS. 6A and 6B illustrate a caretaker or a medical professional assisting the subject with collecting a clean urine sample using a variation of the urine collection and drainage device.
Figure 6B:
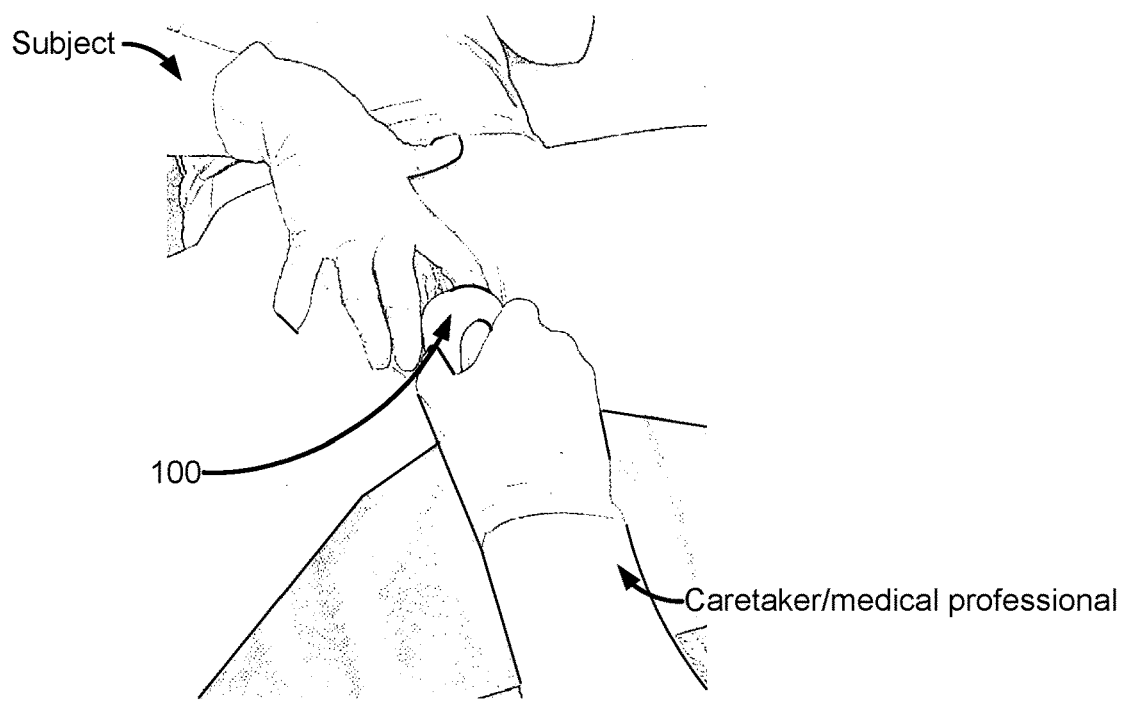
Figure 6C:
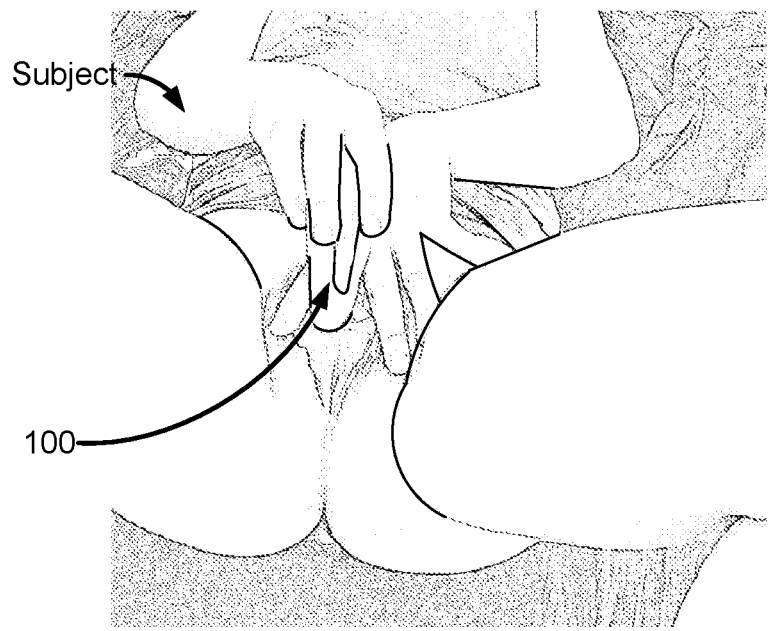
FIGS. 6C and 6D illustrate the subject using the urine collection and drainage device to collect her own clean urine sample.
Figure 6D:
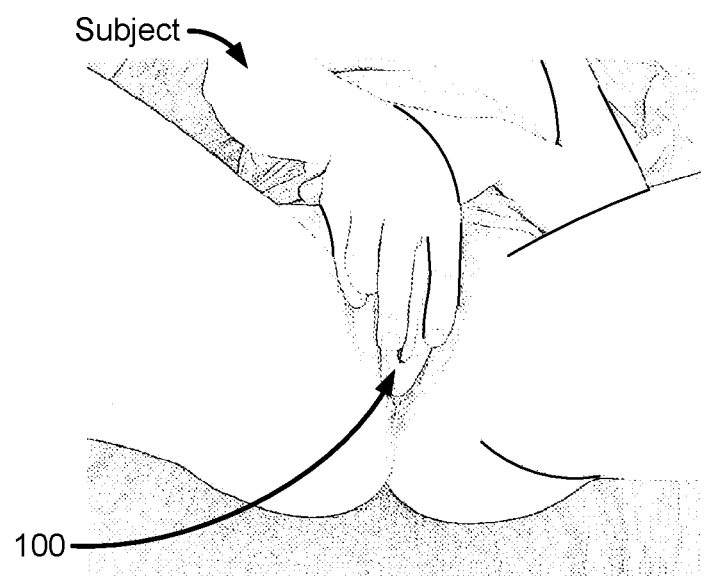

FIGS. 6A and 6B illustrate a caretaker or a medical professional assisting the subject with collecting a clean urine sample using the urine collection and drainage device 100. FIGS. 6C and 6D illustrate the subject using the urine collection and drainage device 100 to collect her own clean urine sample.

In one variation, a method of collecting a clean urine sample from a subject can comprise providing a urine collection device 100 comprising a device body 102 having a vulva-facing portion 104 and a handle portion 106. The vulva-facing portion 104 can comprise a bulbous protuberance 112 atop a posterior ridge 151 at a posterior end 110 of the device body 102 and a partial dome portion 114 in proximity to an anterior end 108 of the device body 102. A urine collection slot 116 can be defined along a urethra-facing side 118 of the vulva-facing portion 104 in between the bulbous protuberance 112 and the partial dome portion 114. The method can also comprise using the bulbous protuberance 112 and/or the posterior ridge 151 to spread apart a labia minora of a subject to expose the urethral-opening of the subject. The method can further comprise positioning the urine collection device 100 such that the urine collection slot 116 surrounds a urethral-opening of the subject, the posterior ridge 151 can rest against the fourchette, the bulbous protuberance 112 rests against at least part of a vaginal opening of the subject, and the partial dome portion 114 rests against the vaginal vestibule while surrounded by the labia minora of the subject. The method can further comprise collecting voided urine from the subject through the urine collection slot 116.

In another variation, a method of collecting a clean urine sample from a subject using one hand. The method can comprise holding a urine collection device 100 using the one hand by placing a base protuberance 144 of a handle portion 106 of the urine collection device 100 in contact with or against a palm of the one hand and grasping a contoured handle groove 146 defined along lateral sides of the handle portion 106 with a plurality of fingers of the one hand. The urine collection device 100 can further comprise a device body 102 having an anterior end 108, a posterior end 110 having a posterior ridge 151 defined thereon, and a vulva-facing portion 104. A urine collection slot 116 can be defined along a urethra-facing side 118 of the vulva-facing portion 104 in between the anterior end 108 and the posterior end 110. The method can comprise using part of the posterior end 110 of the device 100 to spread apart a labia minora of a subject to expose a urethral-opening of the subject. More specifically, the method can comprise using at least one of the posterior ridge 151 and a bulbous protuberance defined atop of the posterior ridge to spread apart a labia minora of a subject to expose a urethral-opening of the subject. The method can further comprise holding the urine collection device 100 in place when the urine collection slot 116 surrounds the urethral-opening of the subject. The method can further comprise collecting voided urine from the subject through the urine collection slot 116.

A number of different variations or aspects of the device have been described. Nevertheless, it will be understood by one of ordinary skill in the art that various changes and modifications can be made to the device without departing from the spirit and scope of the disclosure. Elements of devices, apparatus, and methods shown with any variation are exemplary and can be used in combination or otherwise on other variations within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other variations are within the scope of the following claims and the specification and/or drawings may be regarded in an illustrative rather than a restrictive sense.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure.

I claim:

1. A urine collection and drainage device, comprising: a device body comprising a vulva-facing portion and a handle portion, wherein the device body further comprises an anterior end and a posterior end, wherein the vulva-facing portion comprises a bulbous protuberance at the posterior end and a partial dome portion in proximity to the anterior end, wherein lateral sides of the device body converge at the posterior end to form a posterior ridge; a urine collection slot defined along a urethra-facing side of the vulva-facing portion in between the bulbous protuberance and the partial dome portion, wherein at least one of the bulbous protuberance and the posterior ridge is configured to be used to spread apart a labia minora of a subject to expose a urethral-opening of the subject, wherein the posterior ridge is configured to rest against the fourchette of the subject and the bulbous protuberance is configured to rest against at least part of a vaginal opening of the subject when the urine collection slot surrounds the urethral-opening, and wherein the partial dome portion is configured to rest against part of a vulva vestibule and a labia minora of the subject when the urine collection slot surrounds the urethral-opening; and a drainage opening defined along a base of the device body, wherein the urine collection slot is in fluid communication with the drainage opening through an interior cavity defined within the device body, and wherein the urine collection slot has a slot width and a drainage opening width at the base of the device body, wherein the slot width is smaller than the draining opening width, wherein the internal cavity forms a tapered-cone like shape, wherein the handle portion has a base protuberance, wherein the posterior ridge is between the base of the device body and the bulbous protuberance, and wherein a ratio between a base protuberance radius of curvature and a bulbous protuberance radius of curvature is greater than one.

2. The device of claim 1, wherein the urethra-facing side is curved when viewed from a side of the device, and wherein the vulva-facing portion rests against the vulva vestibule of the subject when the urine collection slot surrounds the urethral-opening and a fluid-tight seal is formed by the labia minora of the subject as the labia minora surrounds the device body.

3. The device of claim 2, wherein the urethra-facing side has a radius of curvature of between about 8.0 cm and about 12.0 cm.

4. The device of claim 2, wherein the urine collection slot is curved when viewed from the side of the device.

5. The device of claim 1, wherein the slot width is between about 0.25 cm and about 1.0 cm.

6. The device of claim 5, wherein the urine collection slot has a slot length, wherein the slot length is between about 1.0 cm and about 5.0 cm.

7. The device of claim 6, wherein a ratio of the slot length to the slot width is between about 3:1 to about 10:1.

8. The device of claim 1, wherein the urine collection slot is bounded by a first sloped lateral surface and a second sloped lateral surface, wherein the first sloped lateral surface and the second sloped lateral surface converge toward one another as the first sloped lateral surface and the second sloped lateral surface approach the urine collection slot.

9. The device of claim 1, wherein the device body has a minimum device height as measured from the base of the device body to a low point along the urethra-facing side, wherein the minimum device height is 4.0 cm.

10. The device of claim 9, wherein the device body has a maximum device width of between about 3.0 cm and 5.0 cm.

11. The device of claim 1, wherein the partial dome portion is positioned inferior or below the bulbous protuberance.

12. The device of claim 1, wherein the bulbous protuberance has a protuberance width wherein the protuberance width is between about 0.5 cm and about 4.0 cm.

13. The device of claim 1, wherein the handle portion further comprises the base protuberance positioned at the anterior end and inferior or below the partial dome portion.

14. The device of claim 1, wherein the handle portion further comprises a contoured handle groove defined along both handle lateral sides, and wherein the contoured handle groove is positioned inferior or below the partial dome portion.

15. The device of claim 1, further comprising a urine collection bag or a urine collection receptacle coupled to at least part of an interior cavity wall of the device body, wherein the urine collection bag or the urine collection receptacle extends through the drainage opening and is configured to receive a clean urine sample.

16. The device of claim 1, wherein the device body has a maximum body length, wherein the body length is between about 7.5 cm to about 12.5 cm.

17. A method of collecting a clean urine sample from a subject, the method comprising: providing a urine collection device comprising a device body having a vulva-facing portion and a handle portion, wherein the vulva-facing portion comprises a bulbous protuberance atop a posterior ridge at a posterior end of the device body and a partial dome portion in proximity to an anterior end of the device body, and wherein a urine collection slot is defined along a urethra-facing side of the vulva-facing portion in between the bulbous protuberance and the partial dome portion, and wherein the urine collection slot has a slot width and a drainage opening width at a base of the device body, wherein the slot width is smaller than the draining opening width, and wherein an internal cavity forms a tapered-cone like shape, wherein the handle portion has a base protuberance, wherein the posterior ridge is between the base of the device body and the bulbous protuberance, and wherein a ratio between a base protuberance radius of curvature and a bulbous protuberance radius of curvature is greater than one; positioning the urine collection device such that the urine collection slot surrounds a urethral-opening of the subject, the posterior ridge rests against the fourchette of the subject, the bulbous protuberance rests against at least part of a vaginal opening of the subject, and the partial dome portion rests against part of the vulva vestibule of the subject and is surrounded by part of the anterior labia minora of the subject; and collecting voided urine from the subject through the urine collection slot.

18. The method of claim 17, further comprising using at least one of the bulbous protuberance and the posterior ridge to spread apart the labia minora of a subject to expose the urethral-opening of the subject.

19. A method of collecting a clean urine sample from a subject using one hand, the method comprising: holding a urine collection device using the one hand by placing a base protuberance of a handle portion of the urine collection device in contact with a palm of the one hand and grasping a contoured handle groove defined along lateral sides of the handle portion with a plurality of fingers of the one hand, wherein the urine collection device further comprises a device body having an anterior end, a posterior end, and a vulva-facing portion, and wherein a urine collection slot is defined along a urethra-facing side of the vulva-facing portion in between the anterior end and the posterior end; wherein the urine collection device further comprises a drainage opening through an interior cavity defined within the device body, and wherein the urine collection slot has a slot width and a drainage opening width at a base of the device body, wherein the slot width is smaller than the draining opening width, wherein the internal cavity forms a tapered-cone like shape, wherein a posterior ridge is between a base of the device body and a bulbous protuberance, and wherein a ratio between a base protuberance radius of curvature and a bulbous protuberance radius of curvature is greater than one; using part of the posterior end of the urine collection device to spread apart a labia minora of a subject to expose a urethral-opening of the subject; holding the urine collection device in place when the urine collection slot surrounds the urethral-opening of the subject; and collecting voided urine from the subject through the urine collection slot.

20. The method of claim 19, further comprising using at least one of the posterior ridge defined along the posterior end and the bulbous protuberance defined atop of the posterior ridge to spread apart the labia minora of the subject to expose the urethral-opening of the subject.

21. The device of claim 1, wherein the handle portion has two handle lateral sides and comprises a contoured handle groove along the two handle lateral sides, wherein the contoured handle groove extends circumferentially around a perimeter of the handle portion.

22. The method of claim 17, wherein the handle portion has two lateral sides and comprises the base protuberance positioned at the anterior end and inferior or below the partial dome portion with a contoured handle groove along the two lateral sides of the handle portion, and wherein the contoured handle groove extends circumferentially around a perimeter of the handle portion.

23. The method of claim 19, wherein the contoured handle groove extends circumferentially around a perimeter of the handle portion.

\* \* \* \* \*